United States Patent
Vroegop

[11] Patent Number: 5,875,778
[45] Date of Patent: Mar. 2, 1999

[54] ELECTRODE FOR STIMULATING AND/OR DETECTING MUSCLE ACTIVITY OF A PATIENT ACCESSIBLE THROUGH A BODY ORIFICE

[75] Inventor: Willem Frederik Vroegop, PT Delft, Netherlands

[73] Assignee: B.V. Optische Industrie 'De Oude Delft', Delft, Netherlands

[21] Appl. No.: 768,081

[22] PCT Filed: Apr. 24, 1990

[86] PCT No.: PCT/NL90/00054

§ 371 Date: Sep. 27, 1991

§ 102(e) Date: Sep. 27, 1991

[87] PCT Pub. No.: WO90/12617

PCT Pub. Date: Nov. 1, 1990

[30] Foreign Application Priority Data

Apr. 26, 1989 [NL] Netherlands .......................... 8901046

[51] Int. Cl.⁶ ...................................................... A61B 5/04
[52] U.S. Cl. ........................... 128/642; 607/138; 128/778
[58] Field of Search ................................... 128/642, 775, 128/778, 780, 733, 639, 641; 607/115, 116, 138

[56] References Cited

U.S. PATENT DOCUMENTS

| | | |
|---|---|---|
| 2,085,644 | 6/1937 | Ferciot . |
| 3,920,003 | 11/1975 | Ash et al. . |
| 4,124,028 | 11/1978 | Gallo . |
| 4,349,031 | 9/1982 | Perlin ...................................... 128/642 |
| 4,785,828 | 11/1988 | Maurer ................................ 128/642 X |
| 4,819,650 | 4/1989 | Goldstein ........................... 128/661.01 |
| 4,909,263 | 3/1990 | Norris ................................. 128/778 X |
| 4,953,563 | 9/1990 | Kaiser et al. ........................... 128/778 |

FOREIGN PATENT DOCUMENTS 0263466 4/1988 European Pat. Off. .

*Primary Examiner*—John P. Lacyk
*Attorney, Agent, or Firm*—Louis E. Marn

[57] ABSTRACT

An electrode assembly for stimulating or detecting activity of muscles accessible through a body orifice includes a carrier member having contact elements electrically connected to a detecting or stimulation assembly and an elongated sheath member formed of a rigid insulating material and having a handle portion and an insertion portion. The insertion portion has electrical contact elements including contact lips extending outwardly from the insertion portion. The elongated sheath member is positioned on the carrier member so that the contact lips are in electrical contact with the contact elements of the carrier member and the contact lips project radially into the sheath member and are resiliently supported in an axial direction against the contact elements of the carrier member.

7 Claims, 2 Drawing Sheets

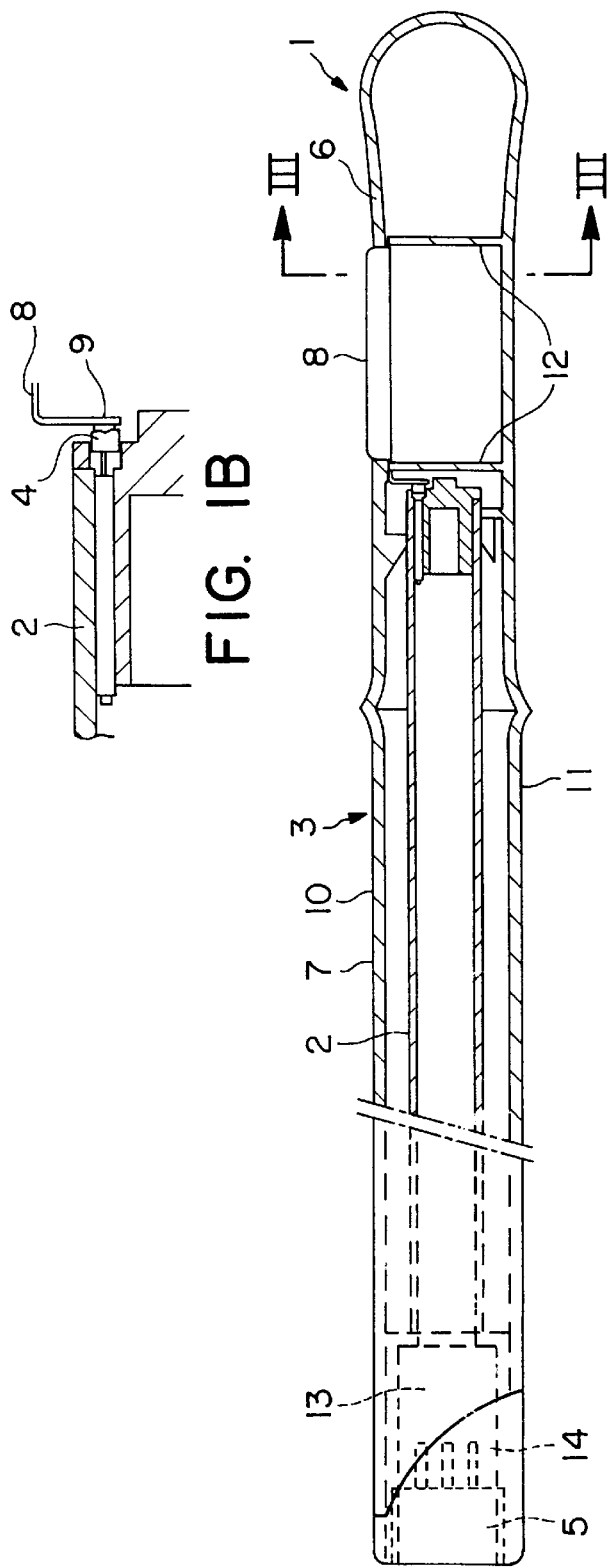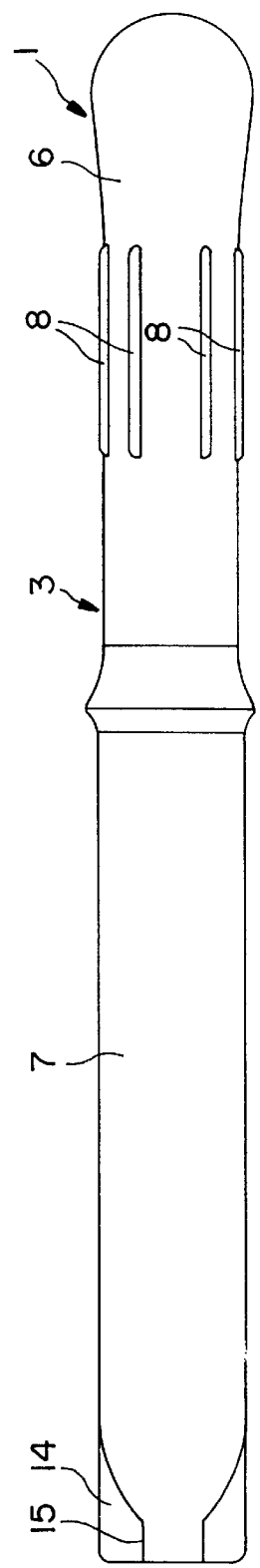

ELECTRODE FOR STIMULATING AND/OR DETECTING MUSCLE ACTIVITY OF A PATIENT ACCESSIBLE THROUGH A BODY ORIFICE

BACKGROUND OF THE INVENTION

1. Field of the Invention

The invention relates to an electrode for stimulating and/or detecting the muscle activity of muscles or muscle groups of a patient which are accessible through a body orifice, the electrode being provided with a carrier and at least two electrically conducting contacts which are connectable by means of a cable to a stimulation and/or detection apparatus.

2. Description of the Prior Art

A known electrode of this type is in the form of a vaginal electrode for stimulating and/or detecting the muscle activity of the pelvic floor muscles in women, in particular the sphincter of the urethra feminina. Incontinence problems in women can be treated in this way. Of course, with the use of such aids it is of great importance to practice good hygiene, in order to prevent infection between patients. In the case of the known electrode for this purpose essentially two possibilities have been used hitherto. A first possibility is to disinfect or, if necessary, sterilize the electrode after each treatment. This is relatively laborious and time-consuming. The second possibility is to give each patient her own electrode, but this calls for a high investment in electrodes. Besides, in this case extensive administration is required, and cleansing of the electrodes is still necessary.

Objects of the Invention

The object of the invention is to provide an electrode of the type mentioned in the preamble, in which the above-mentioned disadvantages are eliminated in a simple, yet effective manner.

SUMMARY OF THE INVENTION

For this purpose, the electrode of the type mentioned in the preamble is characterized according to the invention in that the carrier is provided with contact elements and in that a disposable, elongated sheath of insulating material is detachably connectable to the carrier, while the contacts are situated on the outside of the sheath and are connected to the contact elements when the sheath is fitted on the carrier.

In this way an electrode made up of two parts is obtained, the part coming into contact with the body orifice being disposable after use, so that disinfection or sterilization are no longer necessary. The part which is disposed of after use comprises a simple sheath of insulating material which can be mass-produced at very low cost. The other part, onto which the sheath is pushed, can be made sturdy, and is suitable for use a number of times.

According to a preferred embodiment, the sheath is composed of a rigid plastic material and comprises a part which is adapted in shape to the body orifice, and to which a handle is connected, the contacts being fixed in the sheath and each having a contact lip in the interior of the sheath, which contact lips are in contact with the contact elements when the sheath is fitted on the carrier. An electrode which is easy to handle in practice is obtained in this way.

According to an alternative embodiment, the carrier is made elongated and is provided with a part which is of a shape adapted to the body orifice and has a handle connecting thereto, while the sheath is made of a thin, flexible material.

BRIEF DESCRIPTION OF THE DRAWINGS

The invention is explained in greater detail below with reference to the drawings, in which a number of examples of embodiments are shown schematically.

FIG. 1A is a side view, partially produced in cross-section, of a first embodiment of the electrode according to the invention.

FIG. 1B is a side partially exploded view of an enlarged detail portion of FIG. 1A.

FIG. 2 is a top view of the electrode according to FIG. 1A.

DETAILED DESCRIPTION OF THE INVENTION

Figure 3:
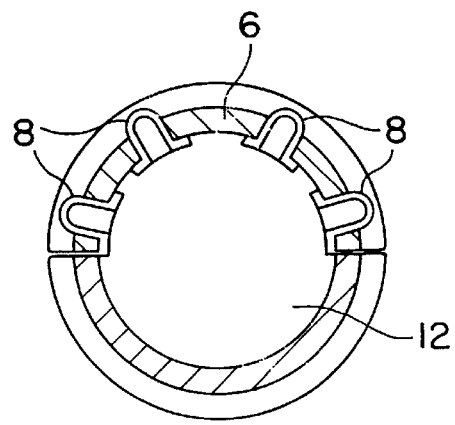
FIG. 3 is a section along the line III—III from, FIG. 1A.

FIGS. 1A–3 show an electrode 1 for stimulating and/or detecting muscle activity of muscles or muscle groups of a patient which are accessible through a body orifice. This electrode 1 is provided with a carrier core 2, in this case in the form of an elongated element, and a sheath 3 which is detachably connectable to the carrier core 2. The carrier core 2 is made of, for example, rigid plastic material and bears on the one end, illustrated in the enlarged detail in FIG. 1A, four contact elements 4 which are supported in a resilient manner in the axial direction in the end of the carrier core 2, and only one of which can be seen in FIG. 1A. The contact elements 4 are connected by conductors (not shown) to a connector 5, which is situated on the other end of the carrier core 2. A cable for connecting the electrode 1 to a stimulation and/or detection apparatus can be connected to the connector 5.

The sheath 3 is made of a rigid plastic material and comprises a part 6 which is adapted in shape to the body orifice, in this case the vagina, and to which a handle 7 is connected, by means of which the electrode is easy to handle and easy to insert into the body orifice. As shown in the cross-section of FIG. 3, four contacts 8 are fitted in the part 6 of the sheath 3, said contacts in this example projecting relative to the outside surface of the sheath 3, so that a good contact with the skin is ensured. The contacts 8 each have at their end a connecting lip 9, these lips projecting radially into the sheath 3 and being pressed against the contact elements 4 when the sheath 3 is slid onto the carrier core 2.

As an alternative, the carrier core 2 can be made considerably shorter, in which case the contacts 8 of the sheath 3 are connected, for example by means of conductors incorporated in the sheath, to connecting lips which are fitted nearer to the open end of the sheath. Of course, differently designed contact elements and connecting lips are also possible.

The sheath 3 is composed of two elongated shell halves 10 and 11, of which the top shell half 10 shown in FIG. 1A has recesses for the contacts 8. The other shell half 11 has two clamping plates 12 which in the assembled state of the sheath 3 fix the contacts 8 in the recesses of the shell half 10.

The carrier core 2 has at the end of the connector 5 a shut-off part 13 of larger diameter which is accommodated in a close fit in the handle 7 of the sheath 3. This shut-off part 13 bears a casing 14 which runs from the side situated opposite the contacts 8 approximately in a circular arc shape to the side where the contacts 8 are situated to a groove 15 formed in the casing 14. The corresponding end of the sheath 3 has a matching shape, by means of which the sliding of the sheath 3 onto the carrier core 2 produces correct positioning of the carrier core 2 and the sheath 3 relative to each other and the contact elements 4 always come to rest against the connecting lips 9 of the contacts 8.

Figure 5:
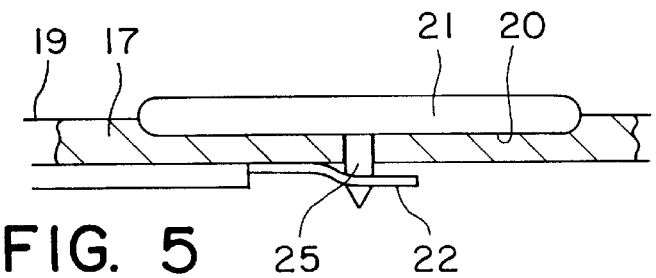
FIG. 5 shows a detail of FIG. 4 on a larger scale.
Figure 4:
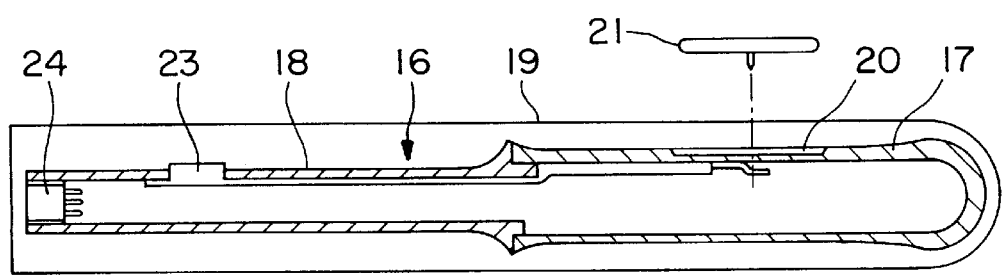
FIG. 4 is a schematically shown longitudinal section of a second embodiment of the electrode according to the invention.

FIGS. 4 and 5 show an alternative embodiment of the invention. In this case the electrode has an elongated carrier 16 which is provided with a part 17 with a shape which is adapted to the body orifice and a handle 18 connecting thereto. In this case use is made of a sheath 19 of a thin flexible material, which in FIG. 4 for the sake of clarity is shown greatly exaggerated at a great distance from the carrier 16, but in practice can lie in a more close-fitting manner around said carrier 16. Recesses 20 for receiving loose contacts 21 are formed in the part 17 of the carrier 16; four of said recesses are again present, and only one can be seen in FIG. 4. Contact elements 22, which are slidable to and fro in the axial direction by means of a button 23, are fitted in the carrier 16. These contact elements 22 are in turn connected, in a manner not shown, to a connector 24 fitted at one end of the carrier 16.

Before use, a sheath 19 is fitted over the carrier 16 and four contacts 21 are pressed into the recesses 20 of the carrier 16. Each contact 21 here has a contact end 25 which pierces through the sheath and is locked on the contact element 22. The sheath 19 is held fast in a sealing manner between the contact 21 and the recesses 20 of the carrier 16, so that the carrier 16 remains insulated from the environment. After use, the contacts 21 can be released again by withdrawing the contact elements 22 with the button 23.

It is pointed out that the contacts 8, 21 in the embodiments described are strip-shaped and are fitted in the axial direction of the electrode. This ensures that even without accurate positioning of the electrode in the body cavity good positioning relative to the sphincters is achieved. It is, however, also possible to use annular or partially annular electrodes.

The shape adapted to the body orifice also means that the electrode remains in place despite any muscle contractions.

Although the above describes an electrode for use in the vagina for stimulating or detecting muscle activity of the sphincter of the urethra feminina, the electrode according to the invention with a suitable shaping can also be used for treatment of the sphincter ani. Put in more general terms, the electrode is suitable for stimulating and/or detecting muscles or muscle groups which are accessible through a body orifice such as, for example, the pelvic floor muscles of a woman.

It can be seen from the above that an electrode is provided with a carrier 2, 16 which is suitable for multiple use, and a sheath 3, 19 which is discarded with the contacts 8, 21 after use. These parts are very simple in design and can be mass-produced at low cost. This means that the electrode described in both embodiments is very suitable for the treatment of patients with incontinence problems, in which case, on the one hand, stimulation of the muscle activity can take place and, on the other, the muscle activity of the muscles or muscle groups, such as the pelvic floor muscles, can be detected. After use, the disposable part 3, 8 or 19, 21 can be thrown away, so that no disinfection or sterilization of the electrode is necessary.

The invention is not limited to the examples of embodiments described above, which can be modified in various ways within the scope of the invention.

I claim:

1. An electrode assembly for stimulating and/or detecting muscle activity of a muscle or muscle groups accessible through a body orifice, which comprises:

a carrier member having contact elements electrically connected to a stimulation and/or detecting assembly; and an elongated sheath member formed of a rigid insulating material and having a handle portion and an insertion portion shaped to said body orifice, said insertion portion having electrical contact elements including contact lips extending outwardly from said insertion portion, said elongated sheath member positioned on said carrier member whereby said contact lips are caused to be in electrical contact with said contact elements of said carrier member, said contact lips project radially into said sheath member and are resiliently supported in an axial direction against said contact elements of said carrier member.

2. The electrode assembly as defined in claim 1 and further including complimentary positioning elements formed on said carrier member and said elongated sheath member.

3. The electrode assembly as defined in claims 1 or 2 wherein said elongated sheath member is comprised of elongated shell half members, one shell half member provided with recesses for positioning said electrical contact elements, another shell half member provided with clamping plates positioned proximate said recesses for fixing said electrical contact elements within said recesses of said one shell half member.

4. An electrode assembly for stimulating and/or detecting muscle activity of a muscle or muscle groups accessible through a body orifice, which comprises:

an elongated carrier member formed of a handle portion and an insertion portion and provided with slidable contact elements electrically connected to a stimulation and/or detecting assembly;

an elongated sheath member formed of a flexible insulating material to be positioned about said elongated carrier member; and electrical contact members for clamping said elongated sheath member to said insertion portion of said elongated carrier member by engaging said contact elements of said elongated carrier member.

5. The electrode assembly as defined in claim 4 wherein said insertion portion of said carrier member is formed with recesses shaped to receive said electrical contact members and said electrical contact member including contact ends for engaging a respective contact element.

6. The electrode assembly as defined in claim 4 or 5 wherein an end of said handle portion of said elongated carrier member remote from said insertion portion thereof is provided with conductors to provide electrical connection to said stimulating and/or detecting assembly.

7. The electrode assembly as defined in claims 4 or 5 wherein said electrical members are strip-shaped and positioned axially about said sheath member.

\* \* \* \* \*